(12) United States Patent
Yanai et al.

(10) Patent No.: US 7,894,887 B2
(45) Date of Patent: Feb. 22, 2011

(54) BIOSIGNAL MEASURING EQUIPMENT

(75) Inventors: Kenichi Yanai, Nisshin (JP); Shinji Nanba, Kariya (JP); Shingo Imura, Kariya (JP); Taiji Kawachi, Kariya (JP)

(73) Assignee: Denso Corporation, Kariya (JP)

( * ) Notice: Subject to any disclaimer, the term of this patent is extended or adjusted under 35 U.S.C. 154(b) by 413 days.

(21) Appl. No.: 12/076,972

(22) Filed: Mar. 26, 2008

(65) Prior Publication Data

US 2008/0243013 A1   Oct. 2, 2008

(30) Foreign Application Priority Data

Mar. 26, 2007   (JP) .............................. 2007-079878

(51) Int. Cl.
*A61B 5/04* (2006.01)
(52) U.S. Cl. .................................... 600/509
(58) Field of Classification Search ................ 600/509, 600/516; 701/1
See application file for complete search history.

(56) References Cited

U.S. PATENT DOCUMENTS

| 3,731,672 | A | * | 5/1973 | McIntosh ................... 600/516 |
| 5,453,929 | A | * | 9/1995 | Stove ............................ 701/1 |
| 6,104,296 | A | | 8/2000 | Yasushi et al. |
| 2004/0230104 | A1 | | 11/2004 | Yanagidaira et al. |

FOREIGN PATENT DOCUMENTS

| JP | Y2-7-3347 | 1/1995 |
| JP | A-07-059738 | 3/1995 |
| JP | A-10-201726 | 8/1998 |
| JP | A-2000-014653 | 1/2000 |
| JP | A-2000-060805 | 2/2000 |
| JP | A-2001-037735 | 2/2001 |
| JP | A-2002-085360 | 3/2002 |
| JP | A-2003-052658 | 2/2003 |
| JP | A-2003-111738 | 4/2003 |

OTHER PUBLICATIONS

Office Action dated Dec. 2, 2008 in corresponding Japanese patent application No. 2007-79878 (and English translation).
U.S. Appl. No. 12/076,971, filed Mar. 26, 2008, Yanai et al.

* cited by examiner

*Primary Examiner*—George Manuel
(74) *Attorney, Agent, or Firm*—Posz Law Group, PLC

(57) ABSTRACT

A signal-to-noise ratio and measurement precision is increased in electrode units disposed on the left and right sides of a steering wheel. A plurality of electrode units is disposed in the left and right handholds of a steering wheel. The contact impedances of all the electrode units are measured. A pair of left and right electrode units to be used to measure an electrocardiographic signal is designated from among the electrode units whose measured contact impedances are less than or equal to a first threshold. The results of measurement of an electrocardiographic signal by the designated electrode units are added in order to minimize noise. An electrode unit with high contact impedance is used to measure induction noise and remove the induction noise component from the electrocardiographic signal measurement result.

27 Claims, 6 Drawing Sheets

BIOSIGNAL MEASURING EQUIPMENT

CROSS REFERENCE TO RELATED APPLICATIONS

Various exemplary embodiments is related to and claims priority to Japanese Patent Application JP 2007-79878, filed Mar. 26, 2007, and is related to the application entitled "BIOLOGICAL SIGNAL DETECTOR" reference no. 109494-US based on Japanese Patent Application No. JP 2007-079877 filed on Mar. 26, 2007, the entire contents of all of which are incorporated herein by reference the entire contents of which are incorporated herein by reference.

BACKGROUND OF THE INVENTION

1. Field of the Invention

Various exemplary embodiments relates to biosignal measuring equipment and, more specifically to equipment that measures a biosignal associated with a vehicle driver using electrodes mounted in a steering wheel of a vehicle.

2. Description of the Related Art

Conventional measuring equipment that uses a pair of left and right electrode units disposed in a ring portion of a steering wheel or spoke portions thereof, detects a potential difference occurring between electrodes when a vehicle driver holds the electrode units with left and right hands, and thereby measures an electrocardiographic complex of the driver is described, for example, in JP-2000-14653A and JP-2002-85360A. It will be understood that the term "electrocardiographic complex" can be considered to refer, for example, to a specific characteristic or series of characteristics of a measured signal or a waveform that indicate specific conditions related to the cardiographic condition of a subject.

However, the conventional measuring equipment is configured to attempt to measure the electrocardiographic complex of the driver merely by detecting a potential difference occurring between the pairs of electrode units disposed on the left and right sides of a steering wheel. Moreover, the left and right electrodes are disposed substantially along the entire periphery of the ring portion or the left and right sides of the spoke portions so that the electrocardiographic complex can be acquired despite a change in the positions on the steering wheel at which the driver holds the steering wheel.

Disadvantages arise however in that in the conventional measuring equipment, electrical noise generated by other electronic equipment mounted in a vehicle and ambient electrical noise existing in the vehicle can be induced into the measuring equipment through the left and right electrode units. Moreover, when an electrocardiographic signal obtained through each electrode unit is weak, noise components cannot be fully removed even by using a filter specifically configured for noise removal resulting in the problem that a signal-to-noise ratio of a finally obtained electrocardiographic complex cannot be increased to such an extent that a potentially abnormal cardiac condition or precursor thereof can be identified.

SUMMARY OF THE INVENTION

In accordance with various exemplary embodiments, the foregoing problems and disadvantages are addressed. An object of various exemplary embodiments is to improve precision in measurement of a biosignal by upgrading a signal-to-noise ratio exhibited by a biosignal that is finally obtained by equipment that measures a biosignal such as an electrocardiographic complex using electrodes disposed on the left and right sides of a steering wheel.

In accordance with exemplary biosignal measuring equipment that is intended to accomplish the above object, multiple electrode units are disposed near each of left and right handholds of a steering wheel. A measuring means measures multiple biosignals via the multiple electrode units, and determines final biomedical complex on the basis of the measured biosignals.

According to the biosignal measuring equipment of various exemplary embodiments, it is possible to select an optimal biosignal, which includes only a little noise component, from among multiple biosignals or to cancel out or minimize noise components included in biosignals by synthesizing the multiple biosignals. Compared with the conventional equipment, the biosignal measuring equipment of various exemplary embodiments can upgrade a signal-to-noise ratio of a finally obtained biosignal so as to improve precision in measurement of a biosignal.

Preferably, the multiple electrode units are disposed in respective areas permitting the palms of the hands of the driver to simultaneously come into contact with the electrode units when the driver holds the left and right handholds.

When a driver holds the handholds in or around which the multiple electrodes are disposed, the pairs of left and right electrode units are used to substantially simultaneously measure multiple biosignals. Consequently, a final biosignal can be determined in a short period of time. The multiple electrode units may be disposed within, for example, a circular area of 15 cm or less in diameter in or around each of the left and right handholds. Moreover, the electrode units may be disposed at positions permitting a driver to easily hold the electrode units when holding the steering wheel. For example, the electrode units may be disposed on the surface of the steering wheel on a driver seat side.

Specifically, when the driver holds the left and right parts of the steering wheel, the roots of the thumbs where the skin is thinnest abut on the surface of the steering wheel on a driver seat side. Consequently, biosignals such as electrocardiographic signals can be readily detected and a signal-to-noise ratio of a biosignal can be increased to increase precision in a measurement of a biosignal.

Parts of the steering wheel that a driver can most readily hold are thought to be the joints between the left and right spoke portions and the ring portion. The electrode units may therefore be disposed near the left and right joint portions where the left and right spoke portions are joined to the ring portion of the steering wheel in the circumferential direction of the ring portion.

When at least one of the electrode units protrudes from the ring portion toward the spoke portion, a contact area in which the palm of the driver comes into contact with the electrode unit is increased and a contact impedance of the palm is decreased. Consequently, a biosignal with less noise can be measured from the electrode unit.

It will be appreciated that, while the measuring means may be located anywhere in a vehicle, the measuring means should be disposed near the electrode units for the purpose of ready wiring and reduction in noise. For example, the measuring means may be mounted in the steering wheel.

In biosignal measuring equipment, each of the electrode units includes a first electrode and a second electrode. The measuring means includes a differential amplification means, an impedance measurement means, a switching circuit unit, and an arithmetic control means. The arithmetic control means connects the electrodes included in each electrode unit to the differential amplification means, impedance measurement means, or a reference potential via the switching circuit unit. Thus, multiple biosignals are measured from a driver and a final biosignal is determined.

Specifically, according to various embodiments of the biosignal measuring equipment, the first electrode and second electrode constituting each of the electrode units disposed on the left and right sides of the steering wheel can be connected to any of the differential amplification means, impedance measurement means, reference potential via the switching circuit unit. Consequently, for example, when the first electrodes of the left and right electrode units are connected to the differential amplification means via the switching circuit unit, an electrocardiographic signal can be measured. When the first electrodes of the left and right electrode units are connected to the impedance measurement means, an impedance associated with a subject, or a subject impedance, can be measured. When the first and second electrodes of each of the electrode units are connected to the impedance measurement means, contact impedances of the hands of the driver relative to the electrode units can be measured.

According to various embodiments of the biosignal measuring equipment, once the action of the arithmetic control means is appropriately designated, the electrode unit suitable for measurement of a biosignal is selected based on contact impedances of the respective electrode units, and an electrocardiographic complex or a subject impedance may be measured. Otherwise, one of the multiple electrode units may be used to measure an induction noise and a noise component can be removed from the result of measurement of the biosignal.

In accordance with the exemplary measuring equipment, multiple sections of differential amplification means that correspond generally to the number of electrode units disposed in each of the left and right handholds should be included. When the arithmetic control means connects each of pairs of left and right electrode units to the associated differential amplification means via the switching circuit unit, the arithmetic control means can simultaneously measure multiple electrocardiographic signals. Consequently, a final electrocardiographic complex can be readily determined from the measured electrocardiographic signals.

Moreover, the switching circuit unit is connected to the left and right electrode units. Therefore, for mounting of the measuring means in the steering wheel, the measuring means may be mounted in the steering wheel with the switching circuit unit separated from the other means such as the differential amplification means, impedance measurement means, and arithmetic control means.

Thereafter, since the arithmetic control means processes a signal sent from the differential amplification means or impedance measurement means so as to determine a final biosignal, arithmetic control means may be realized with a digital arithmetic circuit such as a microcomputer such that the signal sent from the differential amplification means or impedance measurement means can be converted into a digital signal, which can be fetched or the like. It will be appreciated that the circuit lengths from the respective electrode units to the arithmetic control means may be set to at least two or more different lengths.

Specifically, when the circuit lengths from the respective electrode units to the arithmetic control means are identical to each other, noise signals that are induced into the respective electrode units and inputted to the arithmetic control means are in phase with one another. Due to the in-phase relationship, the noise components cannot be cancelled when data samples of the biosignal are added. Therefore the noise is difficult to minimize and a desirable signal-to-noise ratio cannot be obtained, compromising the ability to discern the biosignal.

However, when the circuit lengths from the respective electrode units to the arithmetic control means are different in length, the noise signals that are induced into the respective electrode units and input to the arithmetic control means are out of phase with one another. Consequently, when data samples of a biosignal obtained using the electrode units are added, the noise components can be canceled. Eventually, a signal-to-noise ratio of finally obtained biosignal can be increased.

Further in accordance with exemplary biosignal measuring equipment of various embodiments, the measuring means includes a radiocommunication unit that is used to perform radiocommunication between the biosignal measuring equipment and external equipment. Consequently, according to the measuring equipment, finally obtained biosignal can be transmitted by radio to the external equipment.

The arithmetic control means connects the first and second electrodes that are included in each of the electrode units to the impedance measurement means via the switching circuit unit. The arithmetic control means measures a contact impedance of each of the electrode units using the impedance measurement means. Based on the results of the measurements, the arithmetic control means designates one or more pairs of left and right electrode units for use in measurement of an electrocardiographic complex.

Thereafter, the arithmetic control means switches the connectional destinations of the switching circuit unit so as to connect the first electrodes of left and right electrode units belonging to each of the designated pairs to the differential amplification means, and connect the second electrodes thereof to a reference potential. The arithmetic control means then fetches a signal from the differential amplification means so as to measure one or multiple electrocardiographic signals, and determines a final electrocardiographic complex from the measured electrocardiographic signal or signals.

In the exemplary biosignal measuring equipment in accordance with various embodiments, an electrocardiographic signal can be measured with a small noise component when ones of the left and right electrode units having low contact impedances and with which the palms of the driver are in contact can be used. Consequently, a signal-to-noise ratio of a finally measured electrocardiographic signal can be increased thereby increasing a precision in the finally determined electrocardiographic complex.

When the arithmetic control means measures multiple electrocardiographic signals using multiple pairs of left and right electrode units, the arithmetic control means may perform addition processing on the measured electrocardiographic signals so as to determine a final electrocardiographic complex. In other words, the electrocardiographic signals obtained using the pairs of electrode units are not out of phase with one another, while noise causes a phase difference. Consequently, when the arithmetic control means is configured as described above, electrocardiographic signals can be processed using convolution, additive processing, or the like such that noise components can be canceled out. Eventually, a signal-to-noise ratio of an electrocardiographic complex can be increased.

Moreover, in the exemplary equipment, the first electrode included in each of the electrode units can be connected to the differential amplification means, an impedance measurement means, or a reference potential via the switching circuit unit. Moreover, the second electrode included in each of the electrode units can be connected to the reference potential or impedance measurement means. For measurement of a contact impedance, the arithmetic control means connects all electrodes other than those of the electrode unit that is an object of measurement, to the reference potential via the switching circuit unit. With such a configuration, during measurement of a contact impedance of each of the electrode units, the induction of noise from the other electrode units that could adversely affect the result of the measurement can be prevented.

In the exemplary equipment, when an electrode unit whose measured contact impedance is greater than or equal to a predetermined first threshold is found, the arithmetic control means excludes a pair that includes the electrode unit and an associated left or right electrode unit from the pairs of electrode units to be used to measure an electrocardiographic signal associated with an electrocardiographic complex. For measurement of an electrocardiographic signal using any other pair of electrode units, the arithmetic control means connects the first and second electrodes of the excluded electrode units to the reference potential via the switching circuit unit.

Consequently, only the electrode units whose contact impedances are smaller than the first threshold and that help successfully measure an electrocardiographic signal from a driver can be used to measure the electrocardiographic signal. Therefore, a signal-to-noise ratio of a signal associated with an electrocardiographic complex can be increased and measurement precision can be improved. Moreover, for measurement of an electrocardiographic signal, the first and second electrodes of the electrode units excluded from the measurement are connected to the reference potential. Therefore, noise induction from the unused electrode units can be prevented. Precision in measurement of an electrocardiographic complex can be greatly increased from the above described configuration alone. However, additional increases are possible as will be described. For example, in the exemplary equipment, the arithmetic control means may designate the first threshold on the basis of the results of past measurements of contact impedances.

In the exemplary equipment, when an electrode unit whose measured contact impedance is greater than or equal to a second threshold larger than the first threshold is found on each of the left and right sides, the arithmetic control means connects the first electrodes of the left and right electrode units to the differential amplification means, and fetches a signal from the differential amplification means. Thus, ambient induction noise input into the steering wheel contacts may be measured, and the result of the measurement may be used for determining an electrocardiographic complex. Specifically, when a contact impedance is greater than or equal to the second threshold, it is presumed that a hand of the driver is making only slight contact with the electrode unit and that only ambient induction noise is input into the contact. The induction noise is measured via the differential amplification means by using the correlation between the induction noise and noise present in the electrode unit that is an object of measurement. The result of the measurement is used to remove the induction noise component from a finally obtained electrocardiographic complex. Consequently, a signal-to-noise ratio of signal associated with an electrocardiographic complex can be increased and precision in the measurement can be improved.

In other exemplary biosignal measuring equipment, the arithmetic control means designates a pair of left and right electrode units used to measure an electrocardiographic complex on the basis of the contact impedances of the respective electrode units. Thereafter, the arithmetic control means repeatedly performs a measuring operation of measuring an electrocardiographic signal using the designated pair of electrode units and then determining a final electrocardiographic complex. During execution of the electrocardiographic complex determining operation, the arithmetic control means regularly executes a contact impedance measuring operation at predetermined intervals so as to update the pair of left and right electrode units to be used to measure an electrocardiographic signal associated with an electrocardiographic complex.

According to the equipment, when a driver changes hand position or otherwise re-grips the steering wheel, even if the contact impedances of the respective electrodes are varied due to the change, the electrocardiographic signal measuring operation can be modified accordingly. The electrocardiographic complex can therefore be optimally determined.

It should be incidentally noted that when the measuring means includes a radiocommunication unit, the arithmetic control means may transmit a finally determined electrocardiographic complex to external equipment via the radiocommunication unit. In such a case, not only the electrocardiographic complex but also the contact impedances of the respective electrode units may be transmitted to the external equipment. In addition to the electrocardiographic complex and the contact impedances of the respective electrode units, identification information associated with the left and right electrode units used to measure the electrocardiographic signals may be transmitted to the external equipment.

When the external equipment is used to determine the condition of a driver on the basis of the electrocardiographic complex, the reliability of the electrocardiographic complex can be decided based on the contact impedances of the respective electrode units and the identification information on the left and right electrode units used to measure the electrocardiographic complex, more particularly, the positions of the left and right electrode units retrieved from the identification information. As a result, precision can be increased.

In still other exemplary biosignal measuring equipment, the arithmetic control means performs a subject impedance measuring operation independently of a contact impedance measuring operation and an electrocardiographic signal measuring operation. To be more specific, the first electrodes included in at least one pair of left and right electrode units are connected to the impedance measurement means, and a subject impedance of the driver is measured using the impedance measurement means. Consequently, in addition to a the electrocardiographic complex of the driver, a subject impedance can be measured leading to a determination of additional conditions such as, for example, a body fat percentage or the like.

When the subject impedance is measured as described above, the result of the measurement is affected by the contact impedances of the left and right electrode units. Consequently, in order to measure the subject impedance more precisely, the arithmetic control means may be configured to correct the result of the measurement of the subject impedance using the contact impedances of the left and right electrode units that are used to measure the subject impedance.

Moreover, for measurement of a subject impedance, an arbitrary pair of left and right electrode units may be employed. Alternatively, multiple pairs of left and right electrode units may be used to measure multiple subject impedances. The subject impedances may be subjected to addition processing in order to determine a final subject impedance. Accordingly, precision in measurement of the subject impedance can be increased.

While in some embodiments, a subject impedance can measured independently of an electrocardiographic complex of a driver, in other embodiments, the electrocardiographic complex and subject impedance can be simultaneously measured. Specifically, the arithmetic control means designates a pair of left and right electrode units to be used to measure a signal associated with an electrocardiographic complex, and a pair of left and right electrode units to be used to measure a subject impedance on the basis of the results of measurements of a contact impedance. Thereafter, the arithmetic control means switches the connectional destinations of the switching circuit unit so as to connect the first electrodes included in the left and right electrode units for electrocardiographic signal measurement to the differential amplification means, connect the first electrodes included in the left and right electrode units for subject impedance measurement to the impedance measurement means and connect the other electrodes to the reference potential.

Thereafter, the arithmetic control means fetches a signal from each of the differential amplification means and impedance measurement means. As a result, measurement of an electrocardiographic signal associated with an electrocardiographic complex and measurement of a subject impedance can be simultaneously achieved.

BRIEF DESCRIPTION OF THE DRAWINGS

Other objects, features and characteristics of the present invention will be appreciated and become apparent to those of ordinary skill in the art and all of which form a part of the present application. In the drawings.

DETAILED DESCRIPTION OF THE EXEMPLARY EMBODIMENTS

Various exemplary embodiments will be described below in conjunction with the drawings.

Figure 1:
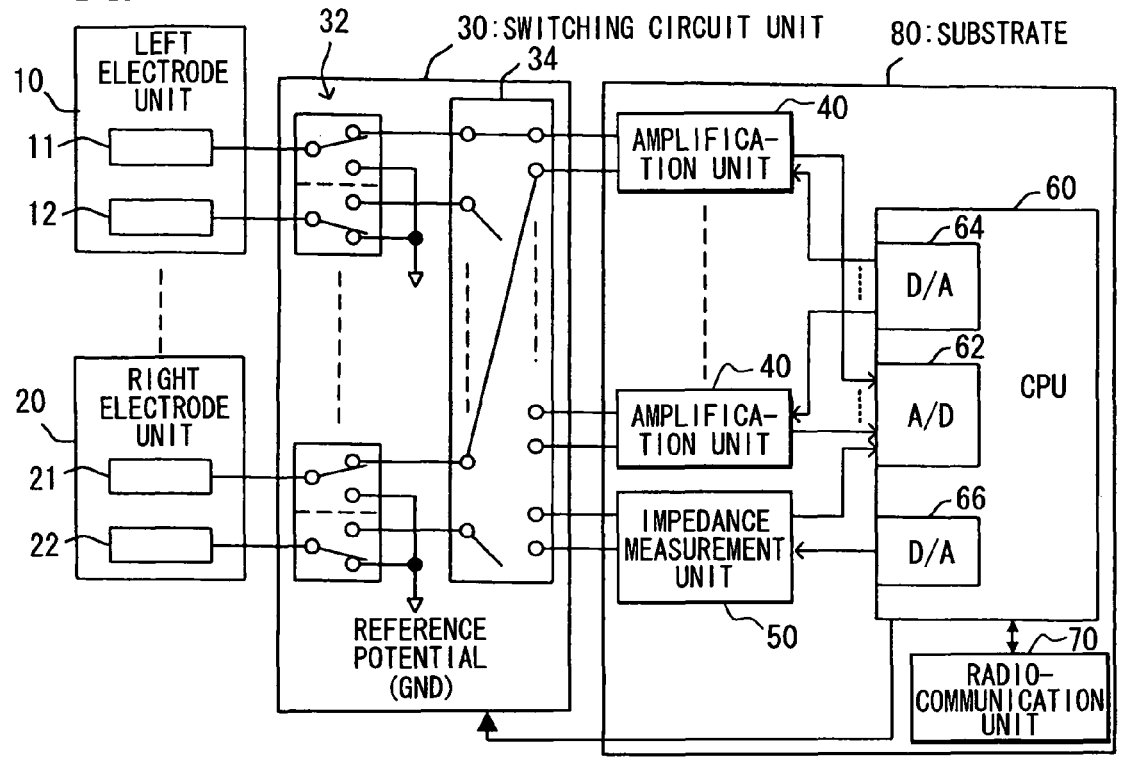
FIG. 1 is a block diagram illustrating an overall configuration of exemplary biosignal measuring equipment in accordance with an embodiment.

As shown in FIG. 1, the biosignal measuring equipment of the present embodiment includes left electrode units 10 and right electrode units 20 that are disposed in or around the left and right handholds of the steering wheel 2 in order to acquire an electrocardiographic signal associated with an electrocardiographic complex from a vehicle driver. It is noted that the terms electrocardiographic signal and electrocardiographic complex are often used interchangeably herein. The electrocardiographic signal can refer to the electrical signal actually measured and the electrocardiographic complex refers to the quantity represented by the signal.

The left and right electrode units 10 and 20 can include multiple electrode units, such as four electrode units in the present embodiment, and are disposed in each of parts of the wheel ring such as ring portion 4 of the steering wheel 2 to which wheel spokes such as left and right spoke portions 6 are joined.

The four left or right electrode units 10 or 20 are disposed in the circumferential direction of the ring portion within, for example, a circular area of 15 cm or less in diameter so that they can be simultaneously held with a left or a right hand. Two center ones of the four left or right electrode units located in the joint of the left or right spoke portion 6 are formed to jut out or otherwise protrude toward the spoke portion 6. The above described configuration is intended to expand an area by which the electrode units come into contact with a hand of the driver when the driver holds the corresponding part of the steering wheel and to thus decrease a contact impedance associated therewith.

Moreover, the electrode units 10 and 20 are disposed on the surface of the steering wheel 2 on a driver seat side and positioned so that when steering wheel 2 is gripped, the roots of the thumbs of the drivers where the skin is thin will come into contact with the electrode units. Positioning the electrodes in such a location is intended to decrease the contact impedances between the hand of the driver and the electrode units 10 and 20.

Moreover, as shown in FIG. 1, each of the electrode units 10 and 20 is constructed as an electrode pair including a first electrode 11 or 21 and a second electrode 12 or 22. The electrodes 11, 12, 21, and 22 of the electrode units 10 and 20 are connected to a measurement circuit unit for measurement of an electrocardiographic signal associated with an electrocardiographic complex and a measurement circuit unit for measurement of a contact impedance via a switching circuit unit 30.

Specifically, the biosignal measuring equipment of the present embodiment includes four amplification units 40 connected to the respective pairs of left and right electrodes units 10 and 20. Each of the amplification units 40 amplifies a potential difference occurring between a pair of left and right electrode units 10 and 20 so as to produce an electrocardiographic signal. The biosignal measuring equipment further includes an impedance measurement unit 50 that measures a contact impedance between each of the left and right electrode units 10 and 20 and the palm of the driver. When the first electrodes 11 and 21 of a pair of left and right electrode units 10 and 20 are connected to the amplification unit 40 via the switching circuit unit 30, an electrocardiographic signal can be measured via the amplification unit 40. When the first electrode 11 or 21 and the second electrode 12 or 22 of each of the electrode units 10 and 20 are connected to the impedance measurement unit 50 via the switching circuit unit 30, the contact impedance can be measured via the impedance measurement unit 50.

The switching circuit unit 30 includes a first selection switch 32 that selects for each of the electrode units 20 and 10 whether the electrode 11, 12, 21, or 22 should be connected to a reference potential such as a ground GND potential in the present embodiment, or a measurement circuit unit that includes any of the amplification units 40 or the impedance measurement unit 50. The switching circuit unit 30 also includes a second selection switch 34 that connects the electrodes 11, 12, 21, and 22, which connections are switched to the measurement circuit unit via the first selection switch 32 to any of the four amplification units 40 or the impedance measurement unit 50.

It will be appreciated that switching by the switching circuit unit 30, measurement of an electrocardiographic signal using the amplification unit 40, and measurement of a contact impedance using the impedance measurement unit 50 can all be executed by a microcomputer 60, hereinafter referred to as a CPU composed mainly of a CPU, a ROM, and a RAM and busses connecting the portions.

A radiocommunication unit 70 is connected to the CPU 60. In response to a request from external equipment, such as handheld equipment carried by a driver or on-board equipment connected to the radiocommunication unit 70, the CPU 60 transmits the result of measurement of a contact impedance or an electrocardiographic signal to the external equipment via the radiocommunication unit 70.

Figure 2A:
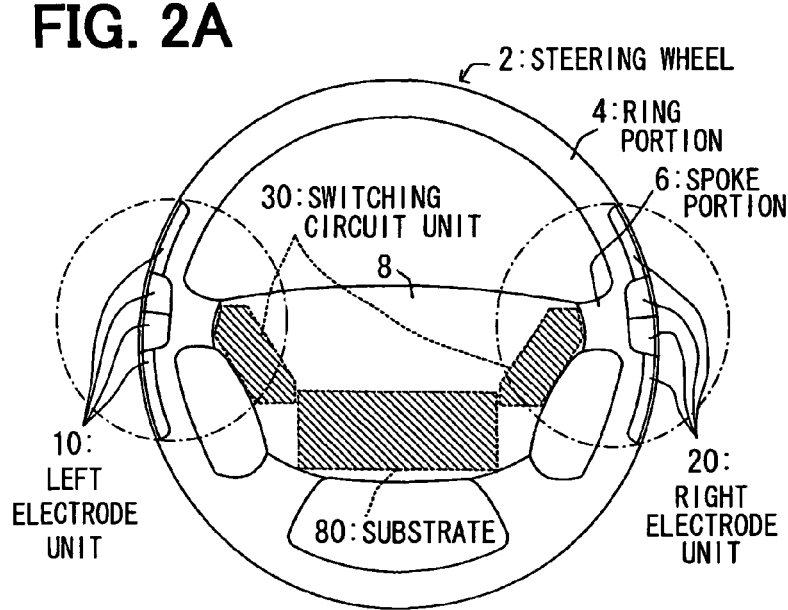
FIG. 2A is a diagram illustrating components of exemplary biosignal measuring equipment disposed in a steering wheel.
Figure 2B:
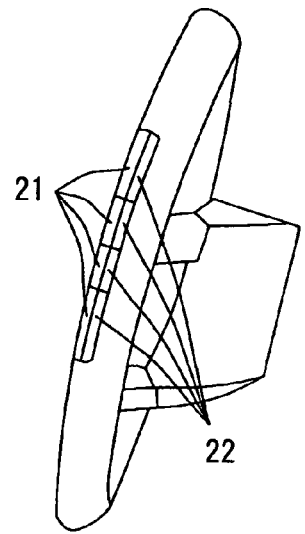
FIG. 2B is a diagram further illustrating components of exemplary biosignal measuring equipment disposed in a steering wheel.

FIG. 2A is a front view of a steering wheel 2 seen from a driver seat side, and FIG. 2B is a side view of the steering wheel. As shown in FIG. 2A, the switching circuit unit 30 is separated into a portion associated with the left electrode unit 10 and a portion associated with the right electrode unit 20, and the portions are disposed on the left and right sides respectively of a center portion 8 of the steering wheel 2 into which an air bag, passive restraint device, or the like is incorporated. The electrode unit 10 including individual electrodes and the electrode unit 20 including individual electrodes are configured to be positioned within a circular area, shown as a dotted line on each of the right and left sides, the diameter being 15 cm or less so as to, for example, increase the likelihood of the driver contacting the electrodes when grasping the steering wheel 2 in standard positions, such as in the area of the handholds. The other circuit units, that is, the four amplification units 40, impedance measurement unit 50, CPU 60, and radiocommunication unit 70 are mounted on a common substrate 80 and incorporated substantially in the center of the center portion 8 of the steering wheel 2.

In the present embodiment, the signal paths of analog signals from the left and right electrode units 10 and 20 to an analog-to-digital (A/D) converter 62 included in the CPU 60 by way of the switching circuit unit 30, amplification units 40, or impedance measurement unit 50 have different electrical lengths. The difference in lengths is intended that noise components introduced through the respective electrode units 10 and 20 and transferred to the A/D converter 62 will be provided with phase differences in order to cancel out noise components, which will converge to a result of measurement, during addition processing to be described later.

Figure 3:
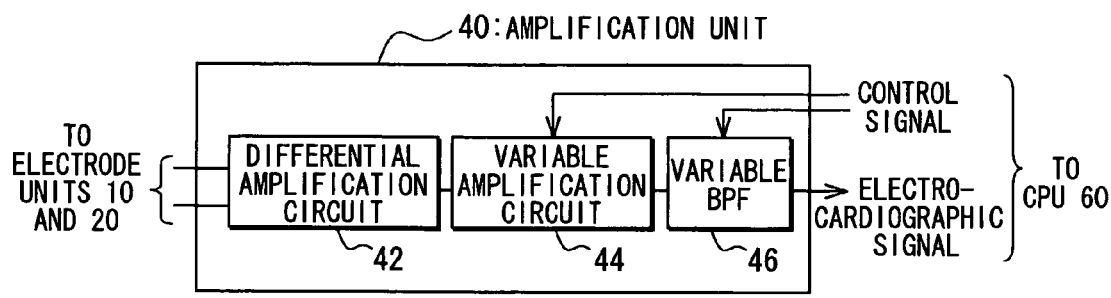
FIG. 3 is a block diagram illustrating a configuration of an exemplary amplification unit.

FIG. 3 illustrates the configuration of the amplification unit 40, which can function as a differential amplification means employed in various exemplary embodiments. The amplification unit 40 includes a differential amplification circuit 42 that detects and amplifies a potential difference occurring between two electrodes connected via the switching circuit unit 30, a variable amplification circuit that produces a controllable gain so as to amplify an output of the differential amplification circuit 42 up to a predetermined level, and a bandpass filter (BPF) 46 that selectively passes a signal, such as an electrocardiographic signal, that falls within a frequency band such as, for example, approximately 35 Hz or less required for measurement of an electrocardiographic complex. It should be noted that the BPF 46 is realized with a variable BPF whose cutoff frequency on a high-frequency side is controllable. The cutoff frequency of the variable BPF 46 and the gain of the variable amplification circuit 44 are controlled with a control signal that is outputted from the CPU 60 via a digital-to-analog (D/A) converter 64.

Figure 4:
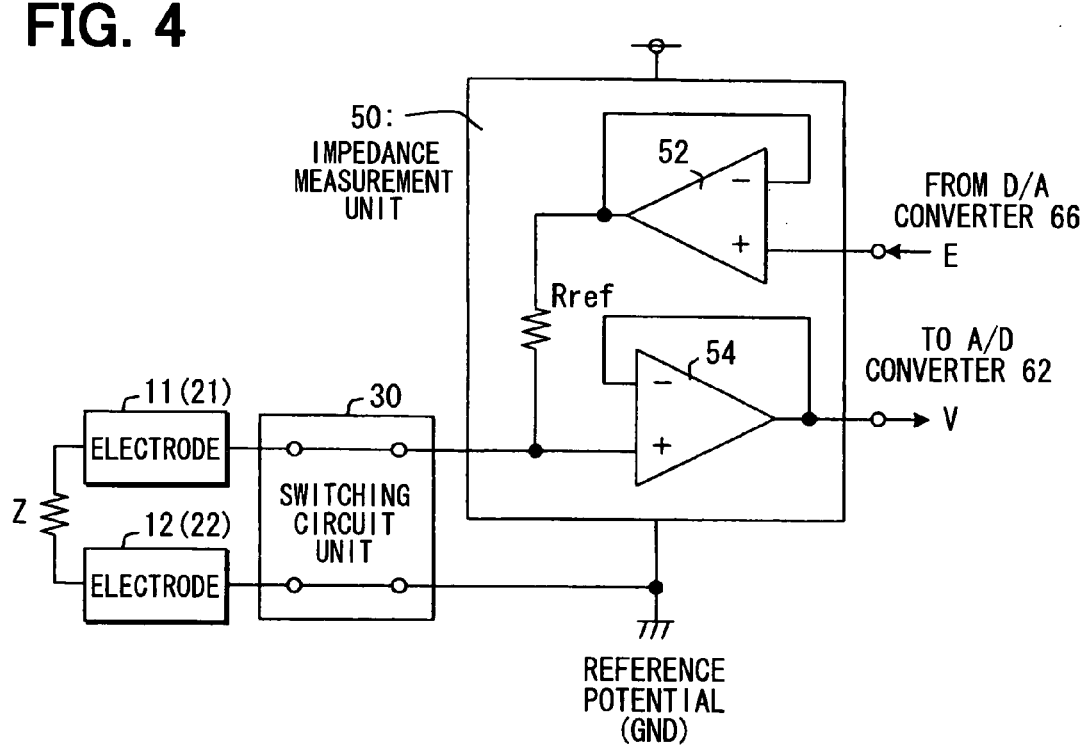
FIG. 4 is a circuit diagram illustrating a configuration of an exemplary impedance measurement unit.

The configuration of impedance measurement unit 50 in the circuit diagram FIG. 4 which can function as an impedance measurement means employed in various exemplary embodiments. In the present embodiment, the impedance measurement unit 50 and arithmetic processing to be performed by the CPU 60 realize the capability of a lock-in amplifier, and an impedance Z between two electrodes such as electrodes 11 and 12, connected via the switching circuit unit 30 is measured.

Specifically, the impedance measurement unit 50 fetches a single-frequency signal E inputted from the CPU 60 via the D/A converter 66 and a buffer 52, and applies the single-frequency signal E to the electrode 11 via a reference resistor Rref. Thus, a fraction of the signal-frequency signal E is produced using the reference resistor Rref and a resistance such as a contact impedance Z between the electrodes 11 and 12. The fractional voltage V is outputted to the CPU 60 via a buffer 54.

The CPU 60 fetches the fractional voltage V via the A/D converter 62, multiplies the single-frequency signal E by the fractional voltage V, uses a low-pass filter to perform filtering processing, and thus obtains the fractional voltage V having noise removed therefrom from a lock-in amplifier mechanism. Further, the CPU 60 uses the voltage V provided by the lock-in amplifier mechanism and the single-frequency signal E to work out a gain G according to the relation of EQ(1)

$$V = G \cdot E \tag{1}$$

and calculates the impedance Z. The arithmetic expression for determining Z is shown in EQ(2)

$$Z = Rref \times G/(1-G) \tag{2}$$

Figure 5:
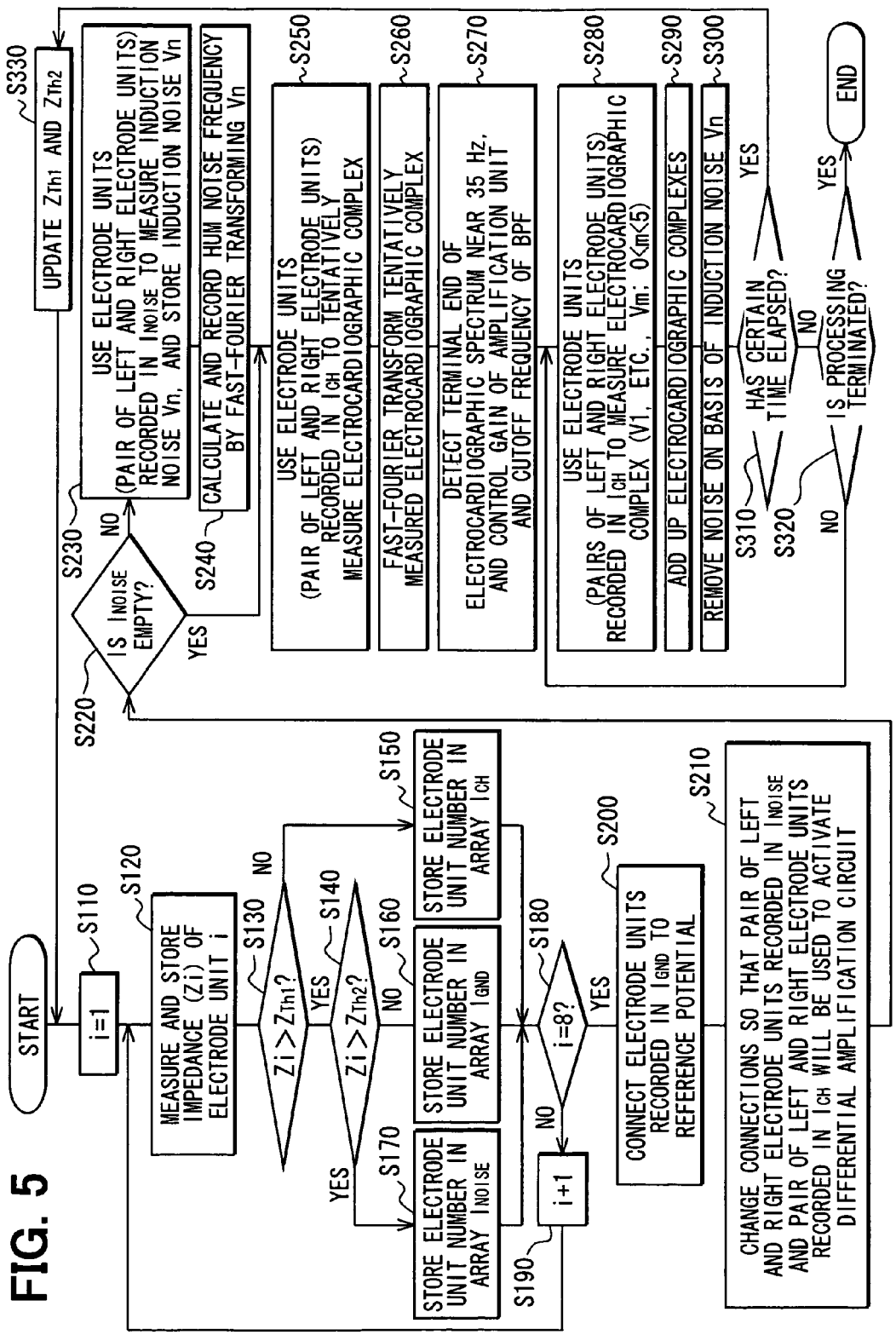
FIG. 5 is a flowchart illustrating exemplary electrocardiogram measurement processing.

As presented in the flowchart shown in FIG. 5, an electrocardiographic complex measurement process to be repeatedly executed by the CPU 50 while, for example, the engine of a vehicle is in operation, is shown and will be described. In accordance with the exemplary processing, an electrode unit discrimination counter i is set to an initial value of 1 at S110 in order to measure a contact impedance at each of four right electrode units 20 and four left electrode units 10.

Figure 6A:
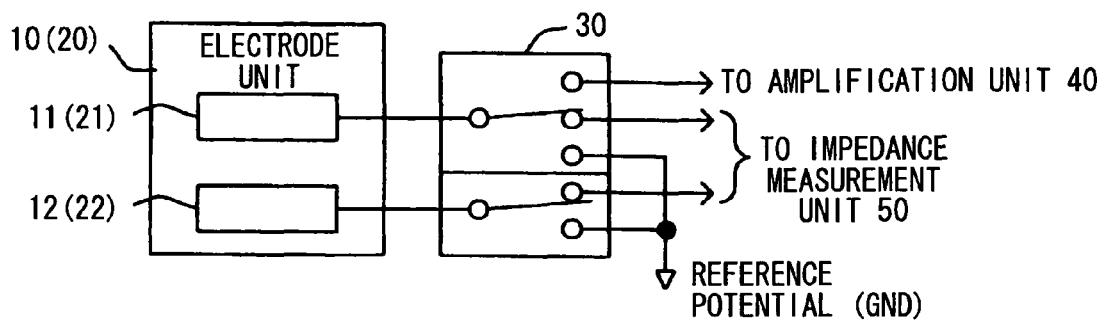
FIG. 6A is a diagram illustrating switching states of an exemplary switching circuit unit associated with contact impedance measurement and electrocardiogram measurement.

At S120 as shown in FIG. 6A, the connections via the switching circuit unit 30 are switched in order to connect the first electrode 11 or 21 of the i-th electrode unit 10 or 20 and the second electrode 12 or 22 thereof to the impedance measurement unit 50. Thereafter, a detection signal, such as the previously described voltage V, is fetched from the impedance measurement unit 50 in order to calculate a contact impedance Zi.

In the processing at S120, stabilization of the detection signal sent from the impedance measurement unit 50 takes a significant time from when the connections to the objects of measurement via the switching circuit unit 30 are switched, for example, in order to connect both the electrodes of the i-th electrode unit 10 or 20 for measurement. Therefore, after the time required for stabilization of the detection signal has elapsed, the detection signal is sampled during a certain period. The sampled detection signals are averaged in order to calculate the contact impedance Zi, which is then stored in the RAM.

As described above, the contact impedance Zi of the i-th electrode unit 10 or 20 is calculated. Thereafter, processing proceeds to S130. A decision is made on whether the contact impedance Zi exceeds a pre-defined first threshold $Z_{Th1}$. When a decision is made that the contact impedance Zi exceeds the first threshold $Z_{Th1}$ corresponding to YES at S130, processing proceeds to S140. A decision is made on whether the contact impedance Zi exceeds a second threshold $Z_{Th2}$ larger than the first threshold $Z_{Th1}$. When the contact impedance Zi is less than or equal to the first threshold $Z_{Th1}$, corresponding to a NO at S130, the i-th electrode unit 10 or 20 is recognized as one to be used to measure an electrocardiographic complex. At S150, the number i of the electrode unit 10 or 20 is stored in an array $I_{CH}$, identifying the electrode as suitable for electrocardiographic measurement, and processing proceeds to S180.

When the contact impedance Zi exceeds the second threshold $Z_{Th2}$, corresponding to YES at S140, it can be presumed that a hand of the driver is not in contact with the i-th electrode unit 10 or 20, and thus the electrode can be used to measure induction noise. Consequently, at S170, the number i of the electrode unit 10 or 20 is stored in an array $I_{NOISE}$, identifying the electrode as suitable for noise measurement, and processing proceeds to S180.

Moreover, when the contact impedance Zi is less than or equal to the second threshold $Z_{Th2}$, corresponding to NO at S140, the contact impedance Zi is sufficiently small that the i-th electrode unit 10 or 20 cannot be used to measure an induction noise. However, the contact impedance Zi is sufficiently large, being greater than $Z_{Th1}$ as described above, that the i-th electrode unit 10 or 20 cannot be used to measure an electrocardiographic complex. Accordingly, at S160, the number i of the electrode unit 10 or 20 is stored in an array $I_{GND}$, identifying the electrode as not suitable for noise measurement and not suitable for electrocardiographic measurement and thus suitable for grounding, and processing proceeds to S180.

Figure 6B:
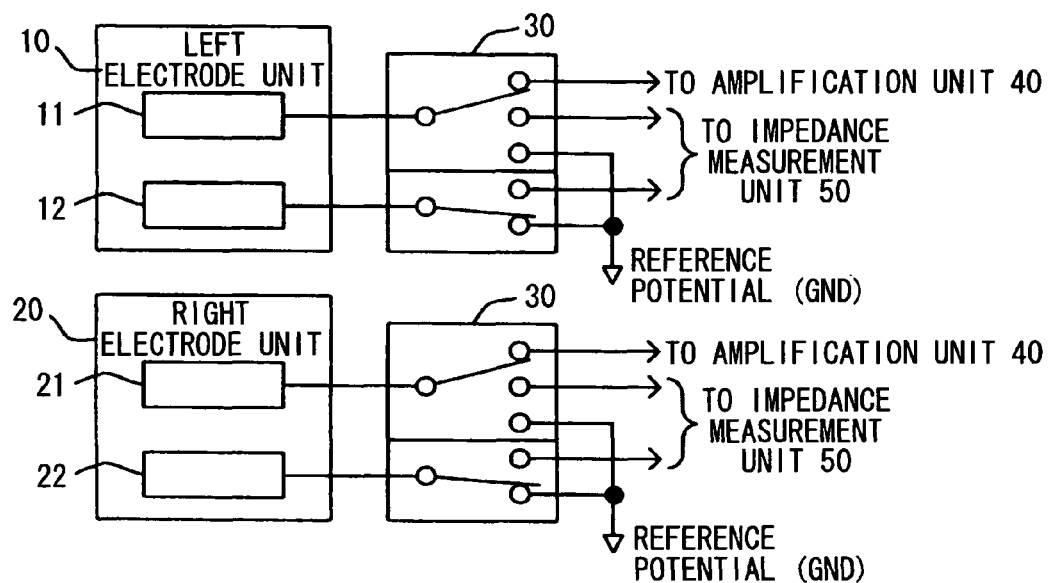
FIG. 6B is a diagram further illustrating switching states of an exemplary switching circuit unit associated with contact impedance measurement and electrocardiogram measurement.
Figure 6C:
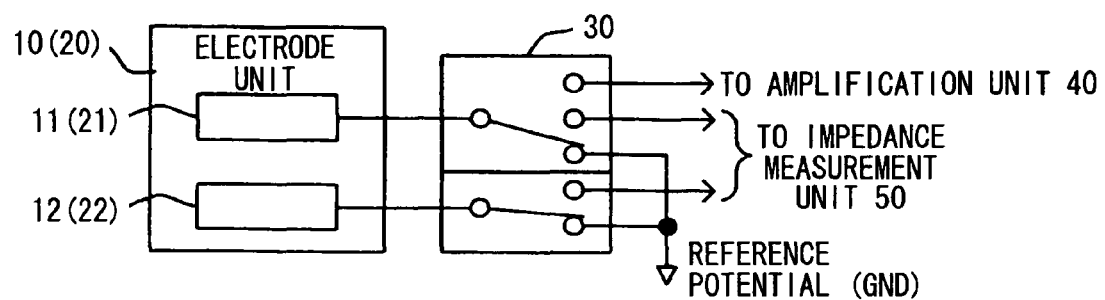
FIG. 6C is a diagram further illustrating switching states of an exemplary switching circuit unit associated with contact impedance measurement and electrocardiogram measurement.

At S180, it is determined whether the value of the counter i has reached 8 in order to make a decision on whether measurement of a contact impedance Zi has been performed on all eight of the electrode units 10 and 20. If the value of the counter i has not reached 8, an electrode unit whose contact impedance Zi should be measured remains and the value of the counter i is incremented by 1 at S190. Thereafter, processing returns to S120. The contact impedance Zi of the i-th electrode unit 10 or 20 is measured. The series of processing from S120 to S170 associated with assigning the number of the electrode unit 10 or 20 to any of the arrays $I_{CH}$, $I_{GND}$, and $I_{NOISE}$ is then executed. When it is determined that the value of the counter i has reached 8, corresponding to YES at S180, processing proceeds to S200. The connections via the switching circuit unit 30 are, as shown in FIG. 6C, switched so that all the electrodes of the electrode units 10 and 20 identified with the numbers i stored in the array $I_{GND}$ will be connected to the reference potential (GND).

When the contact impedance of the i-th electrode unit 10 or 20 is measured at S120, the connections of the electrode units 10 and 20 other than the electrode unit, which is an object of measurement, via the switching circuit unit 30 are switched in the same manner as those at S180 in order to connect all the electrodes of the electrode units 10 and 20 to the reference potential (GND). As described above, the electrodes of the electrode units 10 and 20 other than those that are the object of measurement are connected to the reference potential (GND) in order to prevent noise from being input through the electrodes.

At S210, a pair of left and right electrode units 10 and 20 to be used to measure an electrocardiographic complex is selected from among the electrode units identified with the numbers i stored in the array $I_{CH}$ at S150. A pair of left and right electrode units 10 and 20 to be used to measure an induction noise is selected from among the electrode units identified with the numbers i stored in the array $I_{NOISE}$ at S170. The connections are switched via the switching circuit unit 30, as shown in FIG. 6B, so that the selected pair of left and right electrode units 10 and 20 will be connected to one of the amplification units 40 in order to activate the differential amplification circuit 42. When multiple pairs of left and right electrode units 10 and 20 can be designated at S210 from among the electrode units identified with the numbers stored in the array $I_{CH}$, the pairs of left and right electrode units 10 and 20 are connected to the respective amplification units 40.

Moreover, when an electrode unit that is not available for measurement is paired with one of the electrode units identified as usable based on the numbers stored in the array $I_{CH}$ or $I_{NOISE}$, the usable electrode is connected to the reference potential (GND) in the same manner as those at S200.

If the array $I_{NOISE}$ is not empty, corresponding to NO At S220, then it can be understood that a pair of left and right electrode units 10 and 20 has been selected at S210 from the array $I_{NOISE}$ in which electrode for measurement of induction noise are stored and then connected to the amplification unit 40 and processing proceeds to S230. A signal is fetched from the amplification unit 40 in order to measure an induction noise Vn. The result of the measurement is then stored in the RAM.

During the measurement, the cutoff frequency of the variable BPF 46 included in the amplification unit 40 is maximized. That is, the passband width of the variable BPF 46 is maximized so that a hum noise ranging from about 50 Hz to about 60 Hz and affecting an electrocardiographic complex can be detected. After the induction noise Vn is measured, processing proceeds to S240. The result of the measurement is subjected to fast Fourier transform (FFT) processing. A hum noise frequency ranging from about 50 Hz to about 60 Hz and affecting an electrocardiographic complex is calculated and stored.

When a pair of left and right electrode units 10 and 20 is not selected from the array $I_{NOISE}$, meaning that the array $I_{NOISE}$ is empty, corresponding to YES at S220, or when the processing of S230 and the processing of S240 are executed, processing proceeds to S250. A pair of left and right electrode units 10 and 20 selected from the array $I_{CH}$ is used to tentatively measure an electrocardiographic signal associated with an electrocardiographic complex, or simply an electrocardiographic complex for simplicity. That is, a signal is fetched from the amplification unit 40, to which the pair of left and right electrode units 10 and 20 is connected, in order to tentatively measure an electrocardiographic complex, which includes noise.

At the next S260, the tentatively measured electrocardiographic complex is subjected to FFT processing. At the next S270, a terminal end of an electrocardiographic spectrum near 35 Hz representing the maximum frequency of an electrocardiographic complex is detected based on the result of the FFT processing. Thereafter, the cutoff frequency of the variable BPF 46 and the gain of the variable amplification circuit 44 which are optimal for the amplification unit 40 to remove an unnecessary signal component are calculated based on the result of the detection and the hum noise frequency obtained at S240. The cutoff frequencies of the variable BPFs 46 included in all the amplification units 40 employed for measurement of an electrocardiographic complex and the gains of the variable amplification circuits 44 included therein are controlled according to the result of the calculation.

After the properties of the amplification units 40 employed in measurement of an electrocardiographic complex are controlled, processing proceeds to S280. All of the pairs of electrode units 10 and 20 selected from among the electrode units recorded in the array $I_{CH}$ are used to measure an electrocardiographic complex. At S290, all electrocardiographic complexes measured at S280, such as up to four electrocardiographic complexes in the present embodiment, are subjected to addition processing in order to identify and minimize a noise component to be included in an electrocardiographic complex resulting from the addition processing. At S300, a noise component that results from the addition processing is removed from the electrocardiographic complex according to the induction noise Vn measured at S230.

If only one electrocardiographic complex is measured at S280, such as when only one pair of left and right electrode units 10 and 20 is selected from among the electrodes recorded in the array $I_{CH}$, addition processing need not be performed at S290, but processing proceeds to S300. When the induction noise Vn is not measured at S230, noise removal processing need not be performed at S300, but processing proceeds to S310. Moreover, since a final electrocardiographic complex is obtained at S300, the result of the measurement is stored in the RAM together with the identification information, referred to numbers "i" of the electrode units 10 and 20 employed in the measurement of the electrocardiographic complex.

It is determined whether a predefined certain time has elapsed at S310 since the initiation of the processing of S110. When the certain time has not elapsed, corresponding to NO at S310, processing proceeds to S320. It is determined whether the engine of the vehicle has been stopped and a terminating condition for the electrocardiographic complex measurement processing has been established. When the terminating condition has been established, corresponding to YES at S320, the cardiogram measurement processing is terminated. When the terminating condition has not been established, corresponding to NO at S320, processing returns to S280, and measurement of an electrocardiographic complex continues. When the certain time has elapsed corresponding to YES at S310, processing proceeds to S330 where threshold updating processing including updating the first threshold $Z_{Th1}$ and second threshold $Z_{Th2}$ is executed based on the results of measurements that are the contact impedances of the electrode units 10 and 20. Thereafter, processing returns to S110.

It should be noted that various methods are conceivable for updating of the threshold $Z_{Th1}$ at S330. For example, a method of designating a mean of past contact impedance data items on the basis of past measurement data items of contact impedances, a method of designating a value that is larger by $2\sigma$ than the mean of the past contact impedance data items, a method of designating a value that is a constant multiple of a center value of the past contact impedance data items are conceivable.

As previously described, in the biosignal measuring equipment of the present embodiment, four electrode units 10 and four electrode units 20 are disposed in the left and right handholds of the steering wheel 2, which can be simultaneously held by a driver with left and right hands. For measurement of an electrocardiographic complex, the contact impedances Zi of all the electrode units 10 and 20 are measured, and a pair of left and right electrode units 10 and 20 to be used for measurement of an electrocardiographic complex is designated from among the electrode units whose measured contact impedances Zi are less than or equal to the first threshold $Z_{Th1}$ such as the electrode units recorded in the array $I_{CH}$.

Consequently, according to the present embodiment, the electrode units 10 and 20 whose contact impedances relevant to palms of the driver are so low that an electrocardiographic complex can be successfully measured can be used. Eventually, a signal-to-noise ratio of a finally obtained electrocardiographic complex can be increased, and precision in the measurement can be improved.

In the present embodiment, when multiple pairs of left and right electrode units 10 and 20 can be selected from among the electrode units whose measured contact impedances Zi are less than or equal to the first threshold $Z_{Th1}$ such as the electrode units recorded in the array $I_{CH}$, the pairs of electrode units 10 and 20 are used to measure an electrocardiographic complex. The measured electrocardiographic complexes are subjected to addition processing in order to obtain a final electrocardiographic complex. Consequently, a signal-to-noise ratio of the electrocardiographic complex can be more successfully increased.

In the present embodiment, when electrode units whose measured contact impedances Zi are larger than the second threshold $Z_{Th2}$ are found, a pair of left and right electrode units 10 and 20 for measurement of an induction noise is designated from among the electrodes recorded in the array $I_{NOISE}$, the pair of electrode units 10 and 20 is used to measure an induction noise. A noise component is then removed from an electrocardiographic complex. Accordingly, a signal-to-noise ratio of an electrocardiographic complex can be increased.

Moreover, all the electrodes included in the electrode units 10 and 20 that are unused for measurement of an electrocardiographic complex or an induction noise are connected to the reference potential (GND) in order to prevent invasion of noise through the electrode units 10 and 20. Accordingly, a signal-to-noise ratio of an electrocardiographic complex can be increased.

According to the present embodiment, an electrocardiographic complex with very little noise can be measured. When the result of the measurement is transmitted to external equipment via the radiocommunication unit 70, a cardiac condition can be determined on the external equipment side. Moreover, in the present embodiment, not only a final result of measurement of an electrocardiographic complex is determined but also the identification information such as the numbers i of the electrode units 10 and 20 employed in the measurement of the electrocardiographic complex and the contact impedances of the electrode units 10 and 20 are stored in the random access memory (RAM). The information can be transmitted to external equipment in response to a request inputted from the external equipment via the radiocommunication unit 70.

When a cardiac condition of the driver is determined based on an electrocardiographic complex on an external equipment side, the reliability of the electrocardiographic complex can be decided based on the contact impedances of electrode units and the identification information of left and right electrode units employed in measurement of the electrocardiographic complex, more particularly, the positions of left and right electrode units retrieved from the identification information. As a result, precision in diagnosis of cardiac disease or the like can be increased.

Various exemplary embodiments have been described so far. However it will be appreciated that the invention is not limited to the above described embodiments. Rather, the invention can assume various forms and alternative forms within the various exemplary embodiments.

For example, the biosignal measuring equipment of the aforesaid embodiment has been described as equipment that measures an electrocardiographic complex associated with a biosignal. Since the biosignal measuring equipment includes the impedance measurement unit 50, the impedance measurement unit may be used to simultaneously measure an electrocardiographic complex and a subject impedance.

In accordance with various embodiments, part of measurement processing to be executed by the CPU 60 should be modified as described in connection with FIG. 7. In the exemplary measurement processing, S110 to S270 are executed at S400 in order to perform measurement of a contact impedance of each of electrode units 10 and 20, designation of a pair of left and right electrode units 10 and 20 to be used to measure an electrocardiographic complex or an induction noise, measurement of the induction noise, and control of the gain and cutoff frequency of the amplification unit 40 to be used to measure the electrocardiographic complex.

Figure 8:
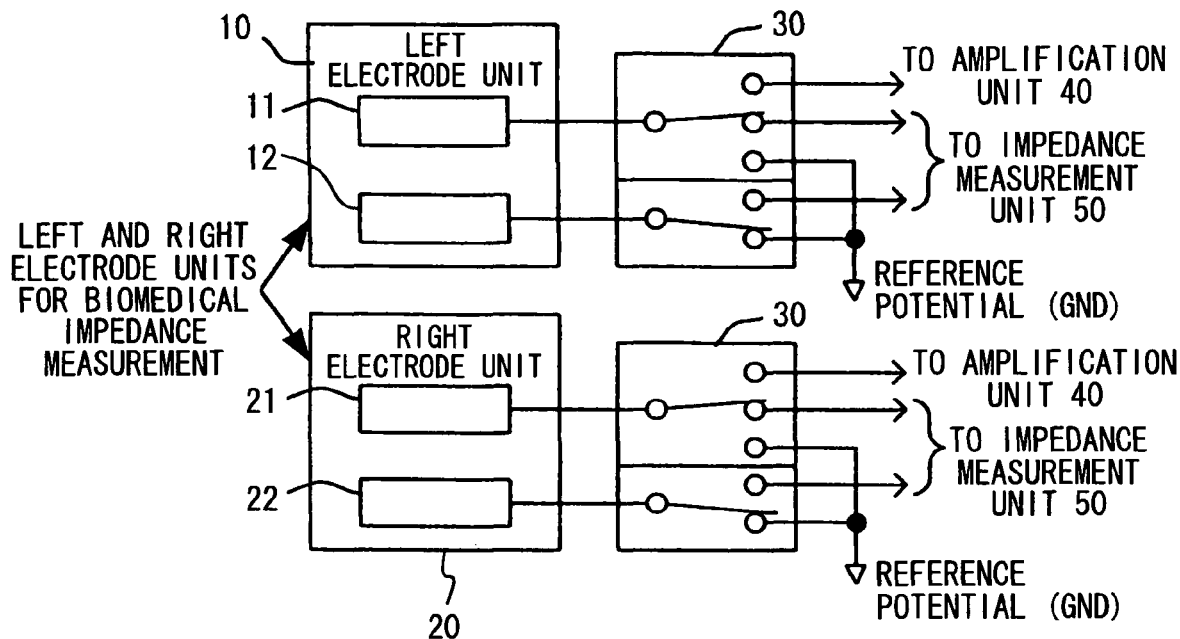
FIG. 8 is a diagram illustrating an exemplary switching state of the switching circuit unit associated with subject impedance measurement.

After the processing of S270 is terminated, it is determined whether both the first and second electrodes of electrode units 20 and 10 are connected to the reference potential (GND), that is whether the electrodes are found recorded in the array $I_{GND}$. If the electrode units 10 and 20 are recorded in the array $I_{GND}$ corresponding to YES at 410, processing proceeds to S420, where the first electrodes 11 and 21 included in the pair of left and right electrode units 10 and 20 recorded in the array $I_{GND}$ are connected to the impedance measurement unit 50. Thus, even though unsuitable for inductance noise or electrocardiographic complex measurement, the pair of left and right electrode units 10 and 20 can be used to measure a subject impedance. The second electrodes 12 and 22 included therein are connected to the reference potential (GND), and processing proceeds to S430. Specifically, the connections via the switching circuit unit 30 are switched as shown in FIG. 8.

At S430, all pairs of electrode units 10 and 20 selected from the electrode units recorded in the array $I_{CH}$ are used to measure an electrocardiographic complex. Moreover, a subject impedance Zb is measured using the impedance measurement unit 50. Incidentally, the measurement of the subject impedance Zb is performed in the same manner as measurement of the contact impedance Zi.

At S440, all the electrocardiographic complexes, such as up to four electrocardiographic complexes in the present embodiment, that are measured at S430 are subjected to addition processing. A noise component included in an electrocardiographic complex resulting from the addition processing is thus minimized. Further, at S450, a noise component based on induction noise Vn measured at S230 and resulting from the addition processing is removed from the electrocardiographic complex.

Thereafter, at S460, the contact impedances of the left and right electrode units 10 and 20 employed in the measurement of the subject impedance Zb are subtracted from each of the subject impedances Zb obtained at S430 in order to thereby correct each of the subject impedances Zb. The corrected subject impedances Zb are stored in the RAM.

A decision is made on whether a predefined certain time has elapsed since the initiation of processing that begins at S110. When the certain time has not elapsed, corresponding to NO at S470, processing proceeds to S480. A decision is made on whether a terminating condition for measurement processing has been established.

When the terminating condition has been established, corresponding to YES at S480, the measurement processing is terminated. In contrast, if the terminating condition has not been established, corresponding to NO at S480, processing returns to S430, and measurement of an electrocardiographic complex and measurement of a subject impedance continue. When it is determined that a certain time has elapsed, corresponding to YES at S470, processing proceeds to S330. After the first threshold $Z_{Th1}$ and second threshold $Z_{Th2}$ are updated, processing returns to S110.

Returning again to the beginning area of processing, when the electrode units 10 and 20 recorded in the array $I_{GND}$ are not found, corresponding to NO at S410, processing proceeds to S510. The first electrodes 11 and 21 included in a pair of electrode units 10 and 20 recorded in the array $I_{CH}$ are connected to the impedance measurement unit 50 and the second electrodes 12 and 22 included therein are connected to the reference potential (GND) as shown for example in FIG. 8, so that the pair can be used to tentatively measure a subject impedance.

At S520, a subject impedance Zb is measured using, for example, the impedance measurement unit 50. At S530, the contact impedances of the left and right electrode units 10 and 20 employed in measurement of the subject impedance Zb are subtracted from the measured subject impedance Zb in order to correct the subject impedance Zb. The corrected subject impedance Zb is stored in the RAM. Thereafter, the first electrodes 11 and 21 included in the electrode units 10 and 20 used to measure the subject impedance Zb are connected to the amplification unit 40 so that the electrode units can be used to measure an electrocardiographic complex. Processing then proceeds to the beginning at S280.

Figure 7:
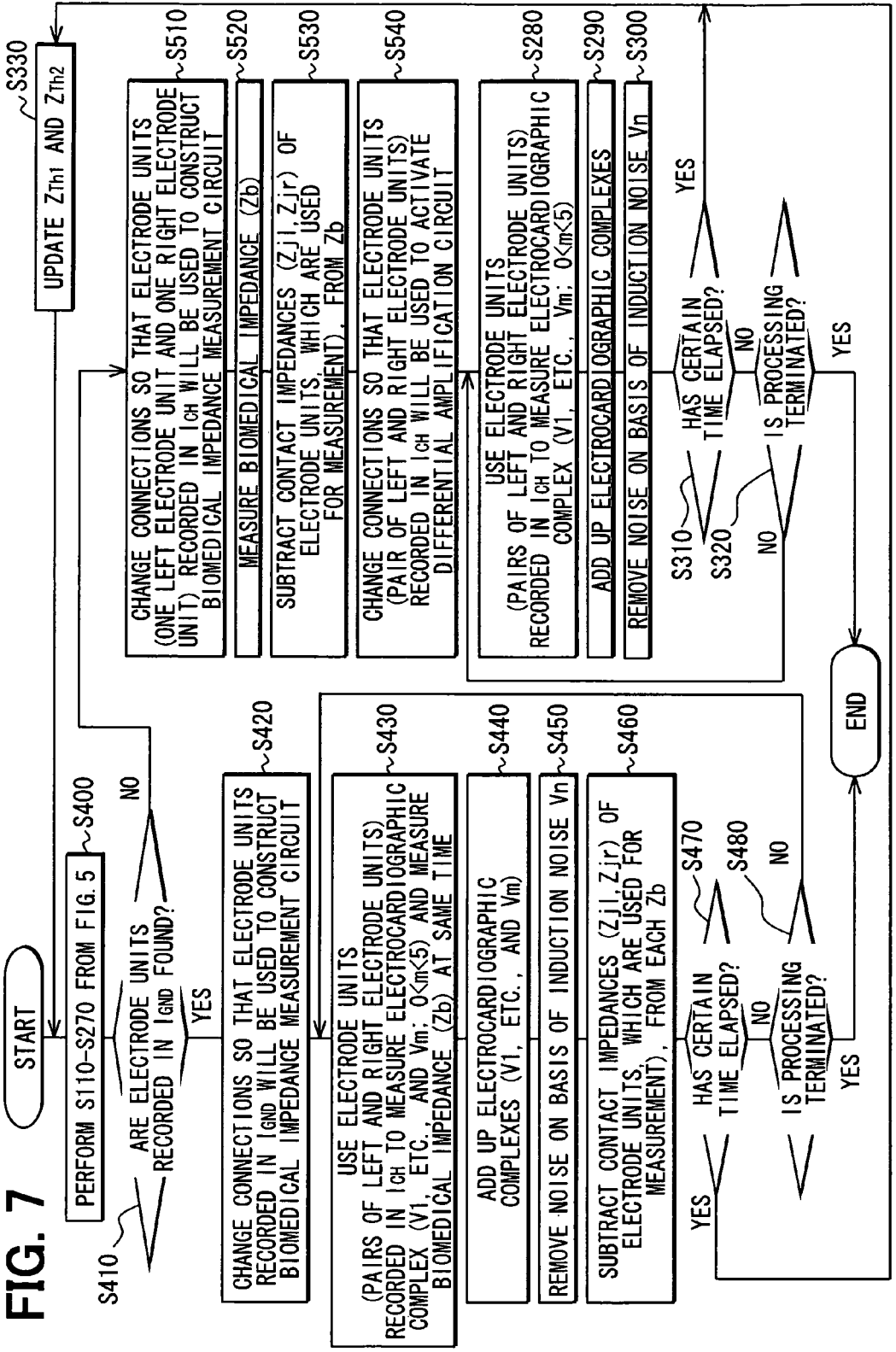
FIG. 7 is a flowchart illustrating exemplary measurement processing for simultaneously measuring an electrocardiogram complex and a subject impedance.

As described thus far, when the CPU 60 executes measurement processing according to the procedure presented in FIG. 7, an electrocardiographic complex and a subject impedance can be simultaneously measured. In the measurement processing presented in FIG. 7, the measured subject impedance is corrected using the contact impedances of the electrode units 10 and 20. Thus, the subject impedance can be highly precisely measured.

What is claimed is:

1. Biosignal measuring equipment comprising:

a plurality of electrode units disposed in left and right positions of a steering wheel; and a measuring means for measuring a biosignal associated with a subject using designated ones of the plurality of electrode units, the subject capable of holding the steering wheel using the left and right positions, wherein the measuring means measures a plurality of biosignals using the designated ones of the plurality of electrode units and determines final information on the basis of the plurality of measured biosignals, wherein each of the plurality of electrode units includes a first electrode and a second electrode; and the measuring means includes:

a differential amplification means for producing a biosignal by amplifying a difference between two input signals;

an impedance measurement means for measuring an impedance between two electrodes;

a switching circuit unit that connects the first and second electrodes of the each of the each of the plurality of electrode units to one of the differential amplification means, the impedance measurement means, and a reference potential; and an arithmetic control means for measuring a plurality of biosignals from the subject by connecting the electrodes of each of the electrode units to the one of the differential amplification means, impedance measurement means, and the reference potential via the switching circuit unit, and for deducing a final complex.

2. The biosignal measuring equipment according to claim 1, wherein the plurality of electrode units are disposed in the left and right positions such that a left palm and a right palm of the subject simultaneously come into contact with multiple ones of the plurality of electrode units when the subject holds the steering wheel.

3. The biosignal measuring equipment according to claim 2, wherein left ones and right ones of the plurality of electrode units are disposed within respective left and right circular areas having a diameter is 15 cm or less, around the left and right positions respectively.

4. The biosignal measuring equipment according to claim 2, wherein:
the plurality of electrode units disposed near left and right joint portions where a ring portion and left and right spoke portions of the steering wheel are joined, the plurality of electrode units disposed in the circumferential direction of the ring portion; and
at least one of the plurality of electrodes is formed to protrude from the ring portion toward the spoke portion.

5. The biosignal measuring equipment according to claim 1, wherein the measuring means is mounted in the steering wheel.

6. The biosignal measuring equipment according to claim 1, wherein the measuring means includes a plurality of differential amplification means, a number of the differential amplification means corresponding to a number of the plurality of electrode units disposed in each of the handholds.

7. The biosignal measuring equipment according to claim 6, wherein the measuring means is mounted in the steering wheel while the switching circuit unit and the means other than the switching circuit unit are separated from one another.

8. The biosignal measuring equipment according to claim 1, wherein:
the arithmetic control means includes a digital arithmetic circuit that converts a signal sent from each of the differential amplification means and impedance measurement means into a digital signal, fetches the digital signal, and performs an arithmetic operation on the digital signal; and
the circuit lengths from the respective electrode units to the arithmetic control means are set to at least two kinds of lengths.

9. The biosignal measuring equipment according to claim 1, wherein the measuring means includes a radiocommunication unit performing radiocommunication between the biosignal measuring equipment and external equipment.

10. The biosignal measuring equipment according to claim 1, wherein:
the arithmetic control means connects the first and second electrodes of the each of the plurality of electrode units to the impedance measurement means via the switching circuit unit so as to measure a contact impedance of each electrode unit using the impedance measurement means;

based on the measured contact impedance, the arithmetic control means designates one or more pairs of left and right electrode units to be used to measure an electrocardiographic signal indicating an electrocardiographic complex;

thereafter, the arithmetic control means switches the switching circuit unit so as to connect the first electrodes of the left and right electrode units belonging to each of the designated pairs to the differential amplification means and connects the second electrodes of the left and right electrode units to the reference potential and fetches a signal from the differential amplification means so as to measure the electrocardiographic signal; and the arithmetic control means determines a final electrocardiographic complex from the measured electrocardiographic signal.

11. The biosignal measuring equipment according to claim 10, wherein after the arithmetic control means uses a plurality of pairs of left and right electrode units to measure a plurality of electrocardiographic signals, the arithmetic control means performs addition processing on the measured electrocardiographic signals so as to determine the final electrocardiographic complex.

12. The biosignal measuring equipment according to claim 10, wherein:
the switching circuit unit is configured to connect the first electrode of each of the electrode units to one of the differential amplification means, the impedance measurement means, and a reference potential, and connect the second electrode of each of the electrode units to one of the reference potential and the impedance measurement means;
the arithmetic control means connects all electrodes other than those of an electrode unit associated with a present measurement, to the reference potential via the switching circuit unit during measurement of the contact impedance.

13. The biosignal measuring equipment according to claim 12, wherein:
when an electrode unit whose measured contact impedance is greater than or equal to a predefined first threshold is found, the arithmetic control means excludes a pair including the electrode unit and an opposite one of the left and right electrode units associated with the electrode unit, from pairs of electrode units for measurement of an electrocardiographic signal;
when any other pair of electrode units is used to measure an electrocardiographic signal, the arithmetic control means connects the first and second electrodes of each of the electrode units that are excluded from the pairs of electrode units for measurement, to the reference potential via the switching circuit unit.

14. The biosignal measuring equipment according to claim 13, wherein the arithmetic control means designates the first threshold on the basis of the results of past measurements of the contact impedance.

15. The biosignal measuring equipment according to claim 13, wherein:
when an electrode unit whose measured contact impedance is greater than or equal to a second threshold larger than the first threshold is found on both the left and right sides, the arithmetic control means connects the first electrodes of the left and right electrode units to the differential amplification means, fetches a signal from the differential amplification means so as to measure an induction noise in the steering wheel and uses the result of the measurement when determining the final electrocardiographic complex.

16. The biosignal measuring equipment according to claim 10, wherein:
after the arithmetic control means designates the pair of left and right electrode units to measure an electrocardiographic signal on the basis of the contact impedances of the respective electrode units, the arithmetic control means continuously performs a measuring operation using the designated pair of electrode units to measure the electrocardiographic signal and determining the final electrocardiographic complex; and
during execution of the electrocardiographic signal measuring operation, the arithmetic control means executes a contact impedance measuring operation regularly at predetermined intervals so as to update the pair of left and right electrode units to be used to measure the electrocardiographic signal.

17. The biosignal measuring equipment according to claim 10, wherein the measuring means includes a radiocommunication unit performing radiocommunication between the biosignal measuring equipment and external equipment, and the arithmetic control means transmits the final electrocardiographic complex to the external equipment via the radiocommunication unit.

18. The biosignal measuring equipment according to claim 17, wherein, in addition to the final electrocardiographic complex, the arithmetic control means transmits the contact impedances of the respective electrode units to the external equipment via the radiocommunication unit.

19. The biosignal measuring equipment according to claim 18, wherein, in addition to the final electrocardiographic complex and the contact impedances of the respective electrode units, the arithmetic control means transmits identification information associated with the left and right electrode units used to measure the electrocardiographic signal to the external equipment via the radiocommunication unit.

20. The biosignal measuring equipment according to claim 10, wherein the arithmetic control means executes, independently of the contact impedance measuring operation and electrocardiographic signal measuring operation, an operation of measuring an impedance of the subject using the impedance measurement means by connecting the first electrodes of at least one pair of left and right electrode units to the impedance measurement means.

21. The biosignal measuring equipment according to claim 20, wherein the arithmetic control means uses the contact impedances of the left and right electrode units used to measure the impedance, to correct the measured impedance of the subject.

22. The biosignal measuring equipment according to claim 20, wherein the arithmetic control means uses a plurality of pairs of left and right electrode units to measure a plurality of subject impedances, and performs addition processing on the plurality of subject impedances so as to determine a final subject impedance.

23. The biosignal measuring equipment according to claim 20, wherein:
the arithmetic control means designates a pair of left and right electrode units to be used to measure the electrocardiographic signal, and a pair of left and right electrode units to be used to measure the subject impedance on the basis of the measured contact impedance;
thereafter, the arithmetic control means switches the switching circuit unit so as to connect the first electrodes of the left and right electrode units for measuring the electrocardiographic signal to the differential amplification means, connect the first electrodes of the left and right electrode units for impedance measurement to the impedance measurement means, and connects the other electrodes to the reference potential; and
the arithmetic control means fetches a signal from each of the differential amplification means and impedance measurement means so as to simultaneously measure the electrocardiographic signal and the subject impedance.

24. An information processing apparatus included in a steering wheel of a vehicle, the apparatus capable of measuring a biosignal associated with a subject that places hands on standard hand positions of the steering wheel while operating the vehicle, the apparatus comprising:
a plurality of electrodes disposed in a left position and a right position of the steering wheel, the plurality of electrodes positioned so as to correspond to the standard hand positions, ones of the plurality of electrodes capable of being formed into a measurement pair that includes one of a left one and a right one of the plurality of electrodes, two left ones of the plurality of electrodes, and two right ones of the plurality of electrodes;
a switching unit coupled to each of the plurality of electrodes, the switching unit connecting two of the plurality of electrodes to form the measurement pair; and
a common unit coupled to the plurality of electrodes and the switching unit, the common unit configured to control the switching unit so as to control the formation of the measurement pair and change the formation of the measurement pair in order to determine a suitability of each of the plurality of electrodes for measurement operations of a biomedical complex associated with the subject based on a first quantity and allocating ones of the plurality electrodes to the measurement operations based on the first quantity, wherein
the common unit is configured to measure one of a plurality of values including biosignals with allocated ones of the plurality of electrodes and to determine final information including a final biomedical complex, the common unit including
a differential amplifier for producing a biosignal by amplifying a difference between the two electrodes that form the measurement pair,
an impedance measurement device for measuring an impedance between the two electrodes that form the measurement pair, and
an arithmetic control device for measuring a plurality of biosignals from the subject by connecting the electrodes to one of the differential amplifier, the impedance measurement device, and a reference potential via the switching unit, and for determining the final complex.

25. The information processing apparatus of claim 24, wherein the first quantity includes a contact resistance associated with each of the plurality of electrodes.

26. The information processing apparatus of claim 24, wherein the one of the plurality of values includes an ambient induction noise, an electrocardiographic signal, and an impedance of the subject.

27. The information processing apparatus of claim 24, wherein the switching unit is configured to couple other ones of the plurality of electrodes not allocated to the measurement operations to the reference potential.

* * * * *